US010716882B2

(12) United States Patent
Evans et al.

(10) Patent No.: US 10,716,882 B2
(45) Date of Patent: Jul. 21, 2020

(54) APPARATUS AND METHODS FOR UNIVERSAL BREAST PUMP KIT (71) Applicant: Ameda, Inc., Buffalo Grove, IL (US)

(72) Inventors: Jeremy Patrick Evans, Vernon Hills, IL (US); Terry Chung, Kildeer, IL (US); Yordan Dimitrov Pargov, Rolling Meadows, IL (US); David Shao Ling, Vernon Hills, IL (US); Joshua Stoia, Wheeling, IL (US); Rodrigo Labrador Gonzales, Lindenhurst, IL (US); Oliver James Harris, Lake Zurich, IL (US); Manshi Kiritkumar Naik, Schaumburg, IL (US); Nathan Meng, Chicago, IL (US); Kwang Suk Kim, Palatine, IL (US)

(73) Assignee: AMEDA, INC., Buffalo Grove, IL (US)

( * ) Notice: Subject to any disclaimer, the term of this patent is extended or adjusted under 35 U.S.C. 154(b) by 204 days.

(21) Appl. No.: 15/914,440

(22) Filed: Mar. 7, 2018

(65) Prior Publication Data

US 2019/0275222 A1 Sep. 12, 2019

(51) Int. Cl.
*A61M 1/06* (2006.01)
(52) U.S. Cl.
CPC ..... *A61M 1/064* (2014.02); *A61M 2205/3337* (2013.01)
(58) Field of Classification Search
CPC .......................... A61M 1/06–066; A61J 13/00
See application file for complete search history.

(56) References Cited

U.S. PATENT DOCUMENTS 2,747,714 A 5/1956 Eason
3,694,020 A 9/1972 Becker et al.
(Continued)

OTHER PUBLICATIONS http://www.hycontrol.com/docs/13-pn-file.pdf; Controlair, Inc., Rolling Diaphragm Air Cylinders (The friction free alternative).
(Continued)

*Primary Examiner* — Manuel A Mendez
*Assistant Examiner* — Courtney B Fredrickson
(74) *Attorney, Agent, or Firm* — Vedder Price P.C.

(57) ABSTRACT

Apparatus and methods for efficient expression of breast milk is provided. The device comprises a horn having a funnel for receiving a breast and a tube extending downwards from the funnel and removably connected to a first end of a main body. The main body has a stem extending downwards from a second end. The horn portion of the device can vary in size depending on the user need to accommodate varying sizes. A flexible cylindrical diaphragm and a valve is provided and are configured to engage and create a sealing between the lower portion of the main body and a container for receiving the breast milk. The use of the cylindrical diaphragm creates minor stress points along the surface of the diaphragm, thereby making it difficult to tear or damage during repeated operation and cleaning. The device further comprises a cap having a port in communication with a pressure source and configured to engage with a container for receiving breast milk, the container further configured to removably connect with the lower second end of the main body. During the milking operation, a negative pressure from the pressure source is communicated through the port to the device in order to create a suction on the funnel for extracting the milk from the breast. In response to the negative pressure, the diaphragm moves from a first state to a second distended state and the valve circumferentially engages and seals around the (Continued)

stem of the main body to provide an airtight seal during the milking operation. Once the negative pressure is released the diaphragm returns back to the first state allowing the milk to freely flow from the horn, through the main body and into the container.

16 Claims, 11 Drawing Sheets

(56) References Cited

U.S. PATENT DOCUMENTS

| | | | |
|---|---|---|---|
| 4,286,668 A | 9/1981 | McCormick | |
| 4,422,835 A | 12/1983 | McKee | |
| 4,484,732 A | 11/1984 | Gould | |
| 4,749,342 A | 6/1988 | Fritsch | |
| 4,773,305 A | 9/1988 | Nissels | |
| 4,827,976 A | 5/1989 | Heimbrodt et al. | |
| 4,924,629 A | 5/1990 | Smith et al. | |
| 5,125,429 A | 6/1992 | Ackroyd et al. | |
| 5,257,572 A | 11/1993 | Jakobi et al. | |
| 5,348,036 A | 9/1994 | Oksanen et al. | |
| 5,373,972 A | 12/1994 | Bystrom et al. | |
| 6,000,416 A | 12/1999 | Kingsford et al. | |
| 6,006,651 A | 12/1999 | Pierce et al. | |
| 6,383,163 B1 | 5/2002 | Kelly et al. | |
| 6,461,324 B1 | 10/2002 | Schlensog | |
| 6,899,530 B2 | 5/2005 | Lehrke et al. | |
| 7,008,400 B2 | 3/2006 | Silver et al. | |
| 7,475,863 B2 | 1/2009 | Donovan | |
| 8,052,635 B1 | 7/2011 | Kelly et al. | |
| 8,070,716 B2 | 12/2011 | Sutrina et al. | |
| 8,137,305 B2 | 3/2012 | Kelly et al. | |
| 8,187,227 B2 | 5/2012 | Luzbetak et al. | |
| 8,591,458 B2 | 11/2013 | Britto et al. | |
| 8,734,385 B2 | 5/2014 | Kliegman et al. | |
| 9,586,734 B2 | 3/2017 | Costello et al. | |
| 9,931,449 B2 | 4/2018 | Evans et al. | |
| 2003/0204164 A1* | 10/2003 | Britto | A61M 1/06 604/74 |
| 2006/0111664 A1* | 5/2006 | Samson | A61M 1/06 604/74 |
| 2007/0060873 A1 | 3/2007 | Hiraoka et al. | |
| 2010/0292636 A1 | 11/2010 | Renz et al. | |
| 2012/0165729 A1* | 6/2012 | Cudworth | A61J 13/00 604/74 |
| 2014/0094748 A1* | 4/2014 | Hong | A61M 1/06 604/74 |
| 2014/0121593 A1 | 5/2014 | Felber et al. | |
| 2016/0256618 A1 | 9/2016 | Embleton | |
| 2016/0346446 A1 | 12/2016 | Evans et al. | |
| 2017/0072119 A1* | 3/2017 | Aalders | A61M 1/06 |

OTHER PUBLICATIONS http://www.swagelok.com/downloads/webcatalogs/EN/MS-02-230.pdf; Swagelok; Pressure Regulators K Series.
http:/www.singervalve.com/hs-fs/hub/230327/file-2358783879-pdf/Whitepapers/Technical_and_Sizing.pdf; Singer Valve; Automatic Control Valves (Technical & Sizing Information).

* cited by examiner

APPARATUS AND METHODS FOR UNIVERSAL BREAST PUMP KIT

RELATED APPLICATIONS

The present disclosure generally relates to a universal breast pump kit and related components. More particularly, the present disclosure relates to a simple, efficient and easy to use universal breast pumping device for expressing breast milk having a lesser number of parts than other similar breast pumping kits currently on the market.

BACKGROUND

Breast pumps are well-known devices for expressing milk from the breasts of users. Breast pumps generally include a breast shield that fits over the nipple, a pump that creates a vacuum to express (or pump) milk, and a detachable container for collecting the expressed milk. However, breast pumps currently on the market consist of numerous silicone parts required to create the necessary suction for expressing milk from the breast.

Breast pumps with numerous silicone parts create difficulty in cleaning the component parts resulting in easily damaged parts during repeated milking operation. Multiple uses of such breast pumps reduces reliability, increases cost and ultimately discourages breast feeding. In addition, most prior art breast pumps comprise separate silicone parts for a diaphragm and a check valve usually in the form of a duck bill design or a flapper. A mother using a breast pump with such configuration will have to spend a lot of time and effort to rinse, wash, disinfect and clean thoroughly each of the pieces, including the separate diaphragm and the valve, in order to reliably use the breast pump for multiple milking operations. Thus, current breast pump designs can easily be damaged during repeated operations and are quite unreliable for repeated use after multiple cleaning cycles.

In addition, contamination from such unreliable breast pumps can affect the health and safety of the mother and the child. Recent studies have shown that there has been a rise in usage of breast pumps due to the increase in percentage of women in the U.S. workforce. Mothers pressed for time between home and work would rather have the convenience to use devices to pump the milk, store the milk and go back to their daily activities without the corresponding hassle of cleaning and protecting from breakage and contamination the numerous silicone parts of those breast pumps.

Therefore, there is a need for a universal breast pump device having less component parts than other conventional breast pumps currently known or used. In addition, there is a need to provide robust design of breast pump components that are not easily damaged during operation of the breast pump or after repeated usage of such device. In order to create a more robust and efficient design for a breast pump, there is a need in the art to develop a reliable breast pump with reduced number of component parts that can overcome the disadvantages of the prior art systems.

SUMMARY OF THE INVENTION

Apparatus and methods for efficient expression of breast milk is provided. The device comprises of a horn having a funnel for receiving a breast and a tube protruding downwards from the funnel and removably connected to a first end of a main body. The main body further comprises a lower second end having a stem extending downwards from the second end. The horn portion of the device can vary in size depending on the need of the user to accommodate varying sizes. All horns are configured to engage with an universal main body that can interact with the rest of the device. A flexible cylindrical diaphragm and a valve is provided and configured to engage and create sealing between the lower portion of the main body and a container for receiving the breastmilk. The use of the cylindrical diaphragm creates minor stress points along the surface of the diaphragm, thereby making it difficult to tear or damage during repeated milking operation and cleaning of the device. The container is further configured to engage with a cap having a port in communication with a pressure source.

At the start of the milking operation, the diaphragm and the container (along with the cap) are removably connected with the lower portion of the main body thereby forming a single unit. During this time, before the start of the milking operation, the diaphragm is in a first (non-expanded) state. During the milking operation, a negative pressure from the pressure source is communicated through the port to the device in order to create a suction on the funnel for extracting the milk from the breast. In response to the negative pressure, the diaphragm moves from the first state to a second distended state and the valve circumferentially engages and seals around the stem of the main body to provide an airtight seal during the milking operation. Once the milking operation is completed and the negative pressure is released, the diaphragm moves back to the first state creating a gap between the valve aperture and the stem of the main body and allowing the milk to flow from the horn through the main body and into the container. The cap and the container containing the expressed milk can then be detached from the rest of the device and stored separately.

BRIEF DESCRIPTION OF THE DRAWINGS

The disclosure will be more readily understood in view of the following description when accompanied by the below drawings. Certain embodiments are shown in the Figures. However, it is understood that the present disclosure is not limited to the arrangements and instrumentality shown in the attached drawings, wherein.

DETAILED DESCRIPTION

The following disclosure as a whole may be best understood by reference to the provided detailed description when read in conjunction with the accompanying drawings, drawing description, abstract, background, field of the disclosure, and associated headings. Identical reference numerals when found on different figures identify the same elements or a functionally equivalent element. The elements listed in the abstract are not referenced but nevertheless refer by association to the elements of the detailed description and associated disclosure.

It is nevertheless understood that no limitation of the scope of the disclosure is hereby intended. Such alterations and further modifications in the illustrated device and such further applications of the principles disclosed as illustrated herein are contemplated as would normally occur to one skilled in the art to which this disclosure relates.

In one aspect of the present disclosure, the device comprises a horn having a funnel for receiving a breast and a tube protruding downwards from the funnel and removably connected to a first end of a main body. The main body further comprises a lower second end having a stem extending downwards from the second end. The horn portion of the device can vary in size depending on the need of the user to accommodate varying sizes. All horns are configured to engage with an universal main body that can interact with the rest of the device. A flexible cylindrical diaphragm and a valve is provided and configured to engage and create sealing between the lower portion of the main body and a container for receiving the breast milk.

In another aspect of the present disclosure, the use of the cylindrical diaphragm creates minor stress points along the surface of the diaphragm, thereby making it difficult to tear or damage during repeated milking operation and cleaning of the device. The container is further configured to engage with a cap having a port in communication with a pressure source. At the start of the milking operation, the diaphragm and the container (along with the cap) are removably connected with the lower portion of the main body thereby forming a single unit. During this time, before the start of the pumping operation, the diaphragm is in a first (non-expanded) state.

In a still further aspect of the present disclosure, during the start of the milking operation, a negative pressure from the pressure source is communicated through the port to the device in order to create a suction on the funnel for extracting the milk from the breast. In response to the negative pressure, the diaphragm moves from the first state to a second distended state and the valve circumferentially engages and seals around the stem of the main body to provide an airtight seal during the milking operation. Once the milking operation is completed and the negative pressure is released, the diaphragm moves back to the first state creating a gap between the valve aperture and the stem of the main body and allowing the milk to flow from the horn through the main body and into the container.

In a still further aspect of the present disclosure, a diaphragm for expressing milk from a breast includes a top side and a bottom side. A flexible membrane built of a resilient material is disposed between the top and the bottom side of the diaphragm. The flexible membrane is capable of expanding and contracting in response to a change in pressure from a pressure source communicated to the diaphragm through the port of the cap. A valve is provided at the bottom of the diaphragm having a flexible wall extending inwardly from a base to define an aperture.

In a still further aspect of the present disclosure, to prevent tear and damages during operation and cleaning, the device comprises a cylindrical shaped diaphragm. A container and a cap is further configured to engage with the diaphragm and a main body for collecting the expressed milk during operation of the device. The cylindrical shape of the diaphragm creates minor stress points along the surface of the flexible membrane making it very difficult to succumb to easy wear and tear during operation and cleaning of the device. The cap and the container containing the expressed milk can then be detached from the rest of the device and stored separately.

In a still further aspect of the present disclosure, during start of the milking operation, a non-uniform gap is designed between the diaphragm and the lower portion of the main body which projects without contact into the diaphragm. The gap is tapered thin at the top and thicker and larger closer to the stem of the main body. This gap is instrumental in efficiently moving the expressed milk through the valve portion of the diaphragm and thereby ensuring smooth operation of the universal breast pumping device.

In a still further aspect of the present disclosure, the diaphragm, with a top and bottom surface, acts as an isolation barrier between the main body and the container. The diaphragm further comprises a thick ring at both the top and bottom and providing a strong sealing when compressed by other kit components. During the milking operation, a negative pressure from the pressure source is communicated through the port to the device in order to create a suction for extracting the milk from the breast. In response to the negative pressure, the diaphragm moves from the first state to a second distended state and creates a vacuum by displacing volume in the milk pathway of the device.

In a still further aspect of the present disclosure, a valve is located at the bottom of the diaphragm. At the start of the milking operation, the diaphragm along with the valve are removably connected with the lower portion of the main body. A container and a cap are further removable connected with the lower portion of the main body thereby forming a single unit for expressing milk. During this time, before the start of the pumping operation, the diaphragm is in a first (non-expanded) state. During the milking operation, a negative pressure from the pressure source is communicated through the port to the device in order to create a suction on the funnel for extracting the milk from the breast. In response to the negative pressure, the diaphragm moves from the first state to a second distended state and the valve circumferentially engages and seals around the stem, extending from the lower portion of the main body, to provide an airtight seal for pumping and collecting the expressed milk. Once the negative pressure (or vacuum) is released, the milk pathway is at atmospheric pressure and the expressed milk can flow freely through the main body, down the diaphragm and into the container.

In a still further aspect of the present disclosure, the main body further comprises a dome-shaped base having a rim and a curved wall having a helical rib extending from the rim downwardly and inwardly to the stem of the main body. An internal surface adjacent to the rim having threads is configured to engage a container used for collecting the expressed milk.

In a still further aspect of the present disclosure, a cap and a container are provided as part of the device for expressing the milk from the breast as well as collecting the expressed milk. The cap has a rim having a planar top portion angled inwardly toward a center axis configured to removably attach with the container. In addition, an inner wall extending from the planar top portion to an annulus has an opening formed adjacent the annulus. The cap further contains a ring wall extending from the annulus and forming a shoulder adjacent the opening. A seal disposed within the ring wall contiguous with the shoulder and a clip to retain the seal against the shoulder is provided with the cap.

Finally, central to operation of the device for expressing milk, a port adjacent to the rim is configured for connection to a pressure source. During the milking operation, a negative pressure from the pressure source is communicated through the port to the device in order to create a suction for extracting the milk from the breast. The container is configured to engage with the cap and has an opening defined by the rim. An external surface adjacent to the rim of the container is configured to engage with the main body of the device used for expressing the milk.

In a still further aspect of the present disclosure, once the milking operation is completed and the negative pressure is released, the cap and the container containing the expressed milk can then be detached from the rest of the device and stored separately. The seal in the cap keeps the milk fresh and contained within the container.

In a still further aspect of the present disclosure, a method for expressing milk from a breast is provided. The method comprises configuring a horn having a funnel adapted for receiving a breast to engage with a first end of a main body and configuring a diaphragm and a valve having a flexible wall extending inwardly from the base to define an aperture to engage with a lower second end of the main body having a stem extending from the lower end. A cap having a port in communication with a pressure source is configured to engage with a container for receiving breast milk and the container is further configured to engage with the lower end of the main body. The container sealingly attaches with the main body to form a single unit at the start of the milking operation. During the milking operation, in response to a negative pressure from the pressure source, the diaphragm is configured to move from the first state to a second distended state circumferentially engaging and sealing the valve aperture around the stem of the main body to provide an airtight seal. Once the milking operation is completed and the negative pressure is released, the diaphragm is configured to move back to the first state, creating a gap between the valve aperture and the stem of the main body, thereby allowing the milk to flow from the horn through the main body and the diaphragm and valve into the container.

These, together with other objects and advantages will be further understood in the details of the construction and operation of the disclosure as more fully hereinafter described below.

Figure 1A:
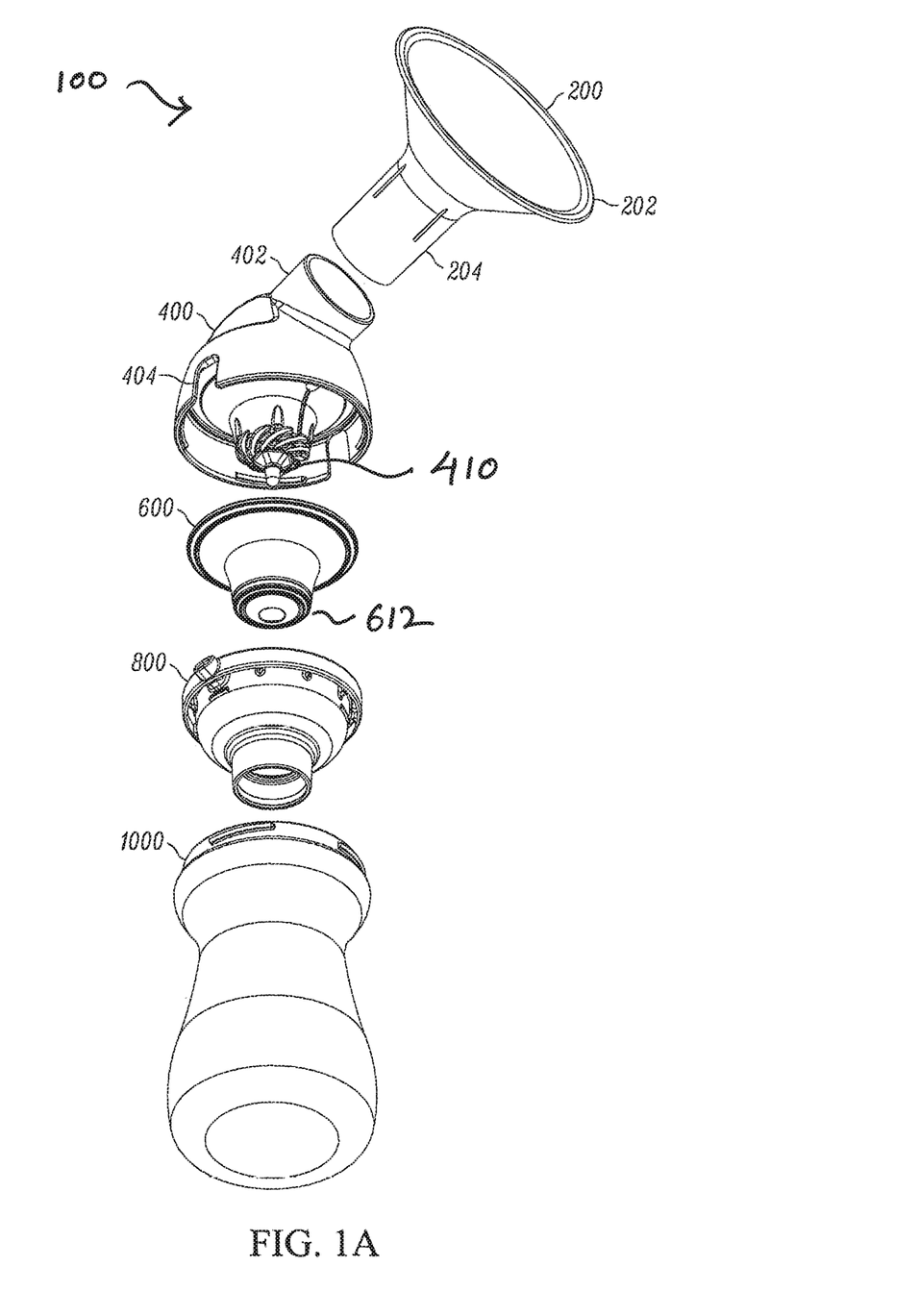
FIGS. 1A-1C is an exploded view of one embodiment of the components comprising the universal breast pump device of the present disclosure.
Figure 1B:
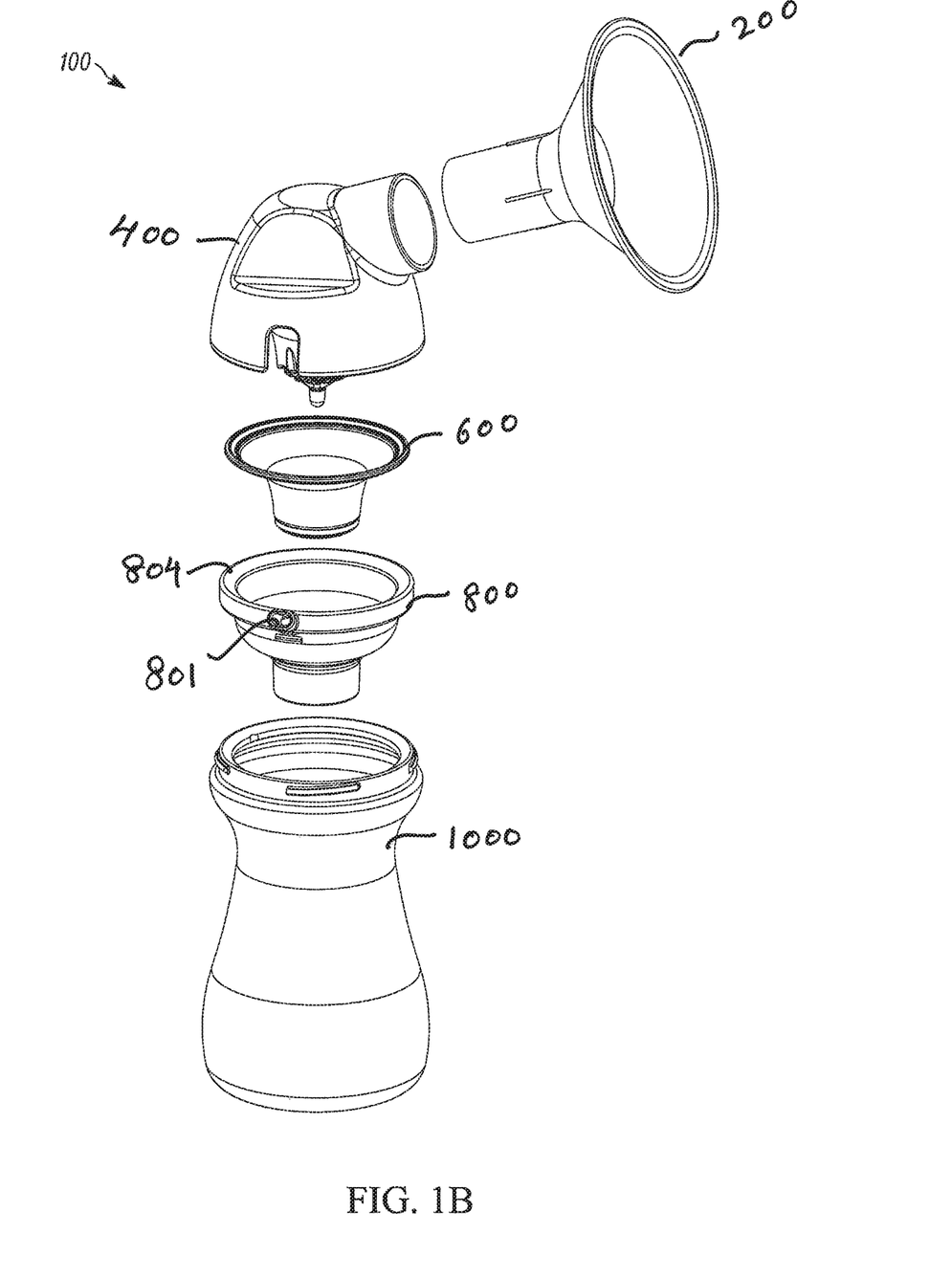
Figure 1C:
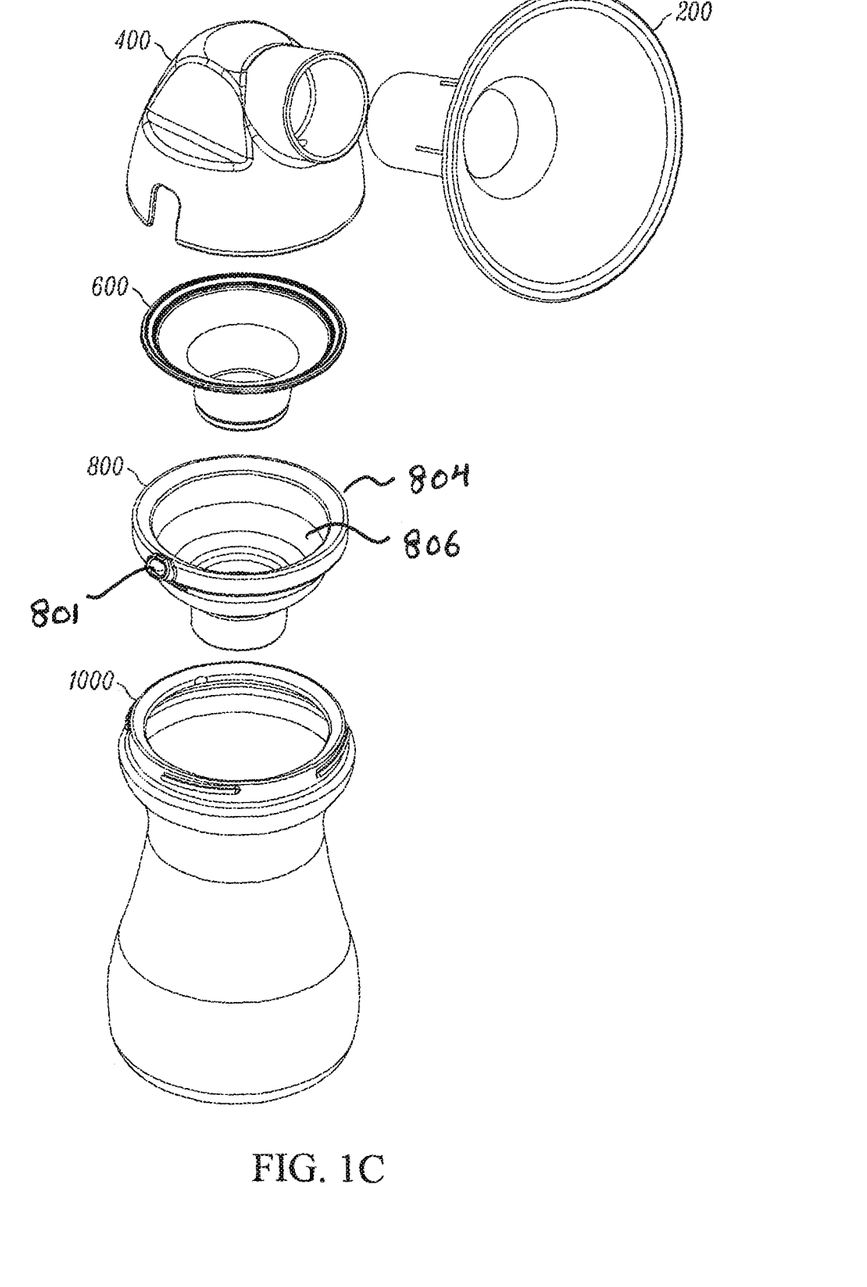

FIGS. 1A-1C illustrate an embodiment of the present disclosure. A device 100 comprises a horn 200 having a funnel 202 for receiving a breast and a tube 204 protruding downwards from the funnel 202 and removably connected to a first end 402 of a main body 400. As further illustrated in FIGS. 1A-1C, the main body 400 further comprises a lower second end 404 having a stem 410 extending downwards from the second end 404 of the main body 400. The horn 200 portion of the device 100 can vary in size depending on the need of the user to accommodate varying sizes. All horns are configured to engage with an universal main body 400 that can interact with the rest of the device 100. A flexible cylindrical diaphragm 600 and a valve 612 is provided and configured to engage and create sealing between the lower portion 404 of the main body 400 and a container 1000 for receiving the expressed breast milk. As further illustrated, the container 1000 is further configured to engage with a cap 800 having a port 801 in communication with a pressure source and configured to engage with the container 1000.

Figure 2A:
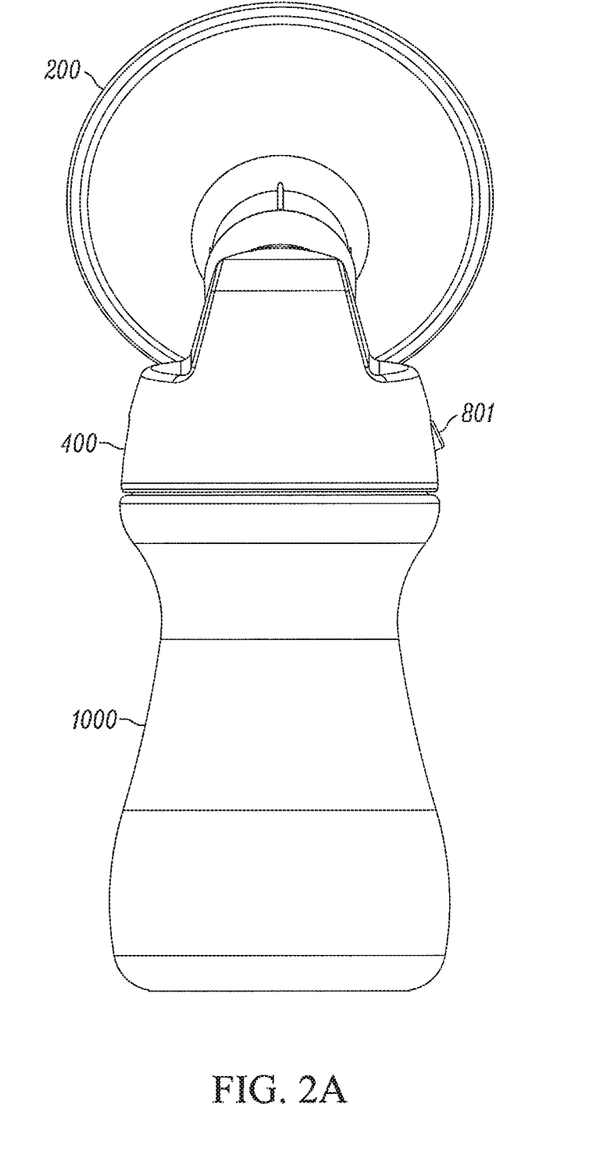
FIGS. 2A-2C is an illustration of the fully assembled universal breast pump device of the present disclosure.
Figure 2B:
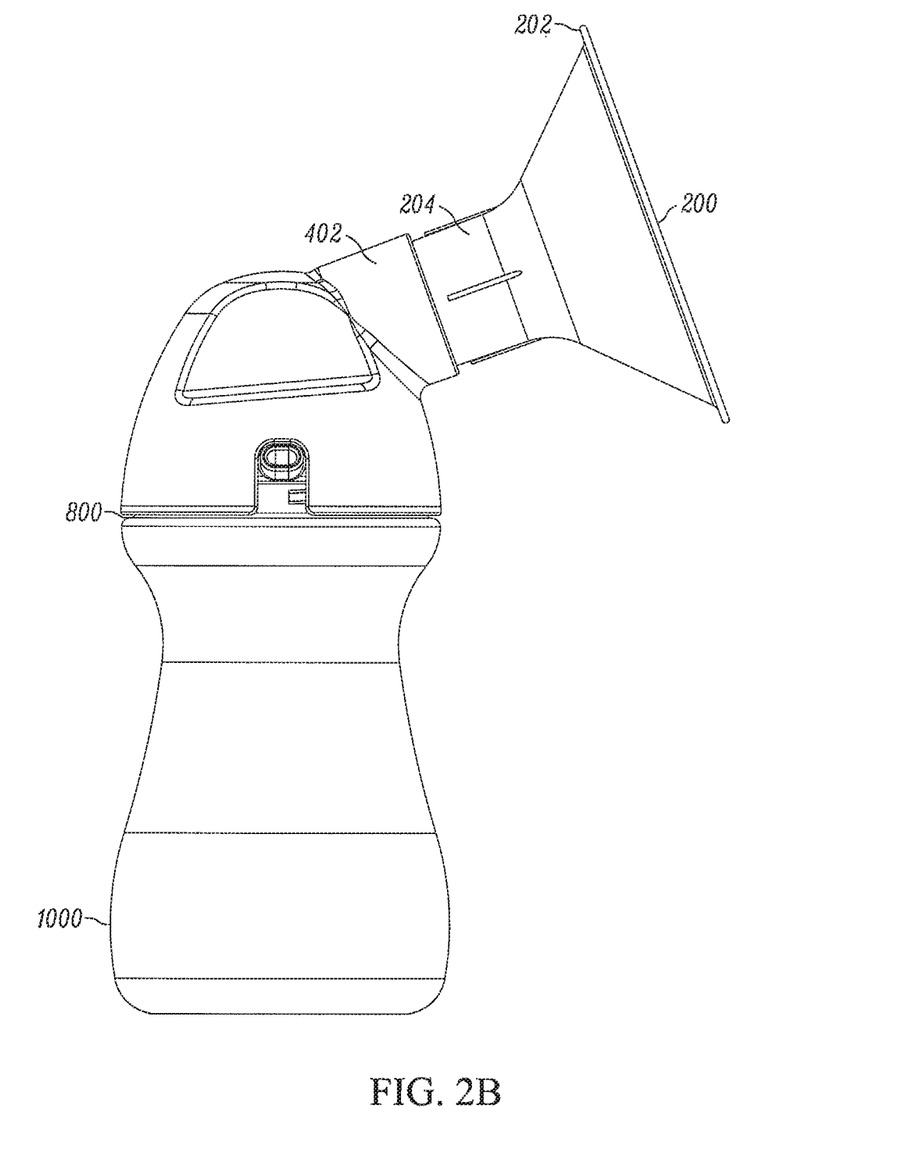
Figure 2C:
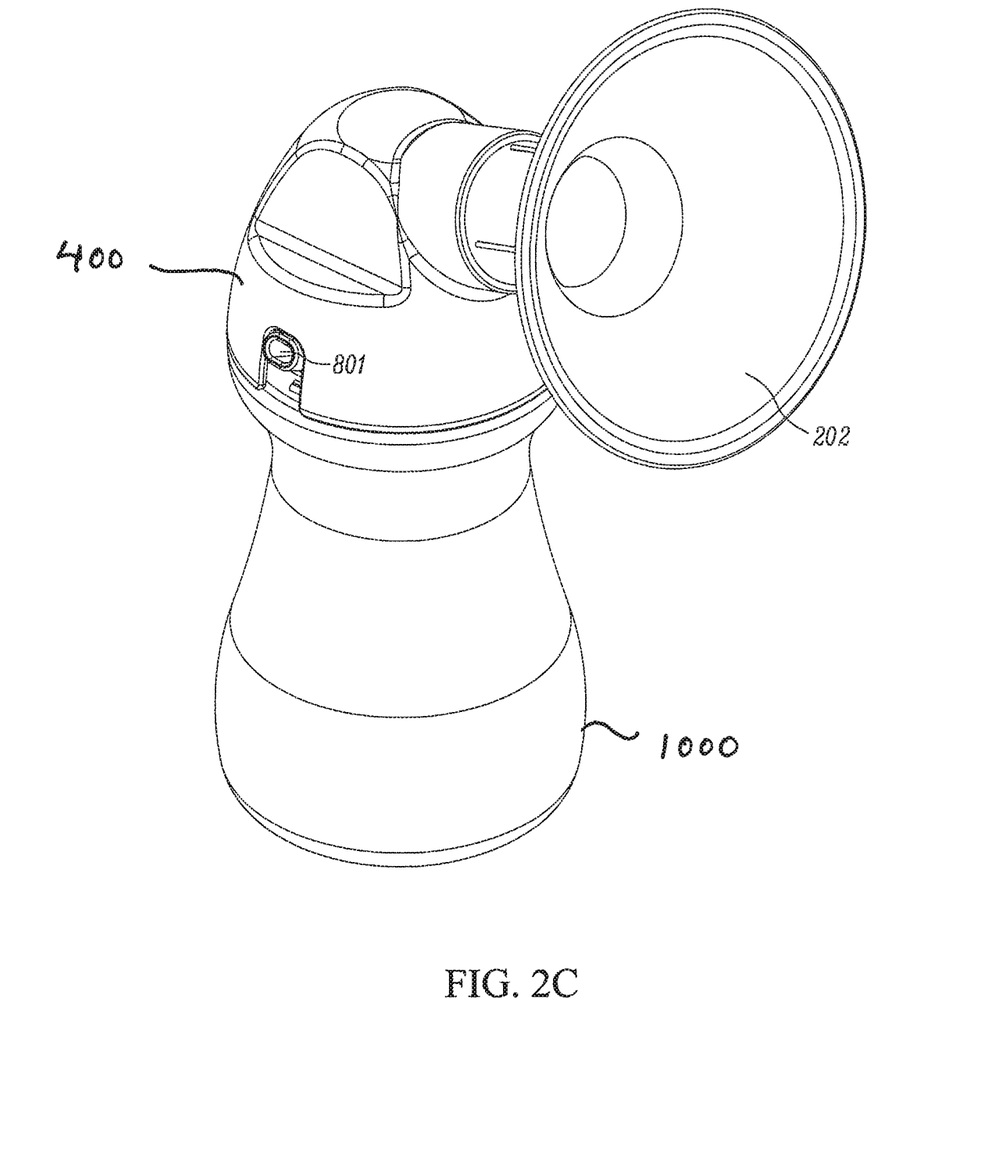
Figure 3A:
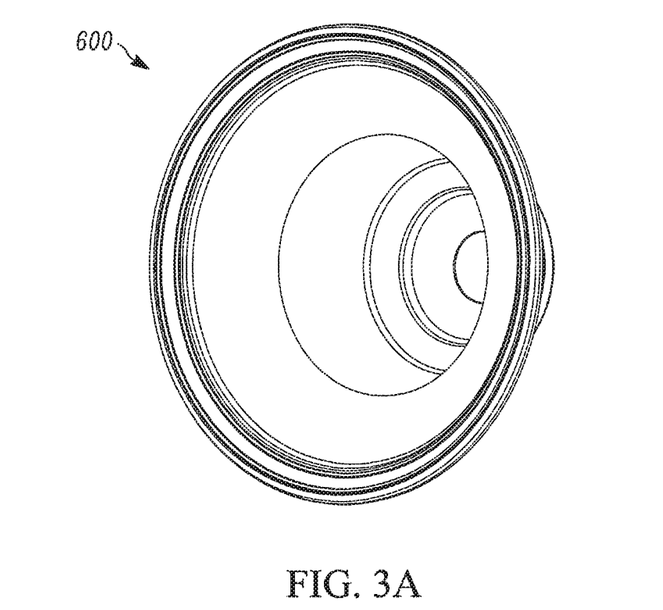
FIGS. 3A-3D are illustrations of one embodiment of the diaphragm used in the universal breast pump device of the present disclosure.
Figure 3B:
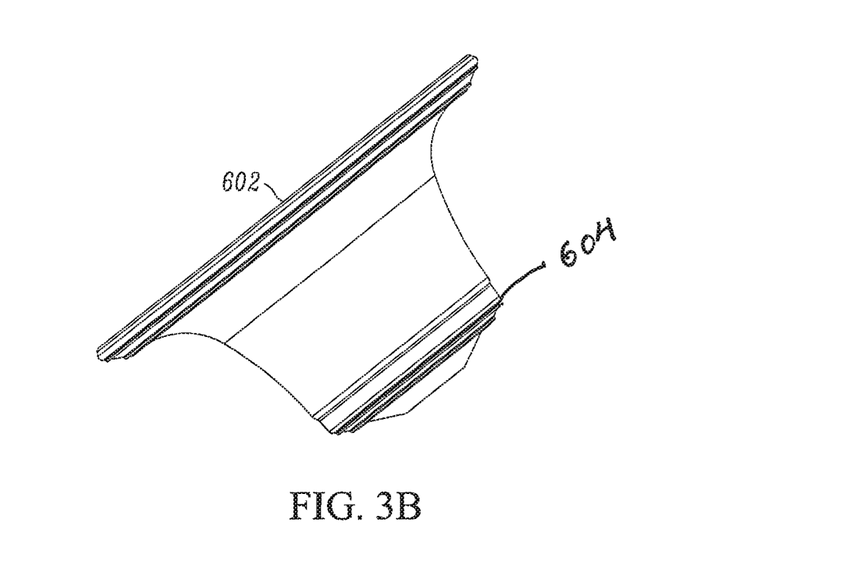
Figure 3C:
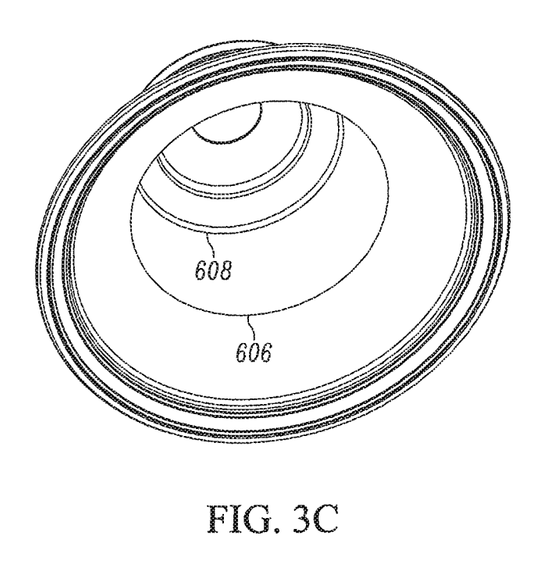
Figure 3D:
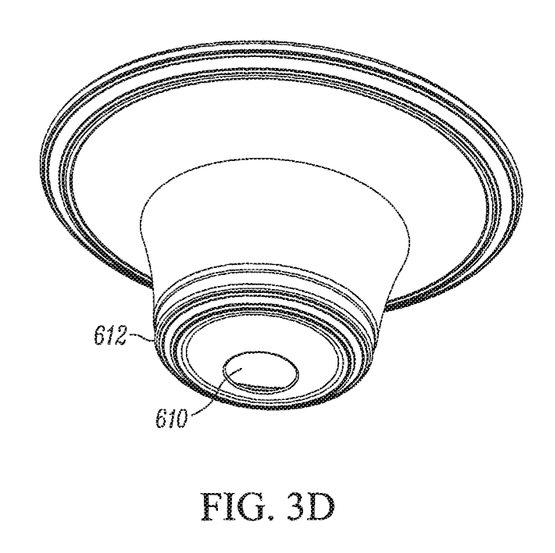

FIGS. 2A-2C illustrates a completely assembled device for use during the milking operation in another embodiment of the present disclosure. As further illustrated, at the start of the milking operation, the diaphragm 600 and the container 1000 (along with the cap 800) are removably connected with the lower portion 404 of the main body 400 thereby forming a complete assemble device 100. The funnel 202 of the horn 200 is adapted to receive the breast of the user. During the milking operation, a negative pressure from the pressure source is communicated through the port 801 to the device 100 in order to create a suction on the funnel 202 for expressing the milk from the breast of the user. Once the milking operation is completed and the negative pressure is released, the expressed milk is allowed to freely flow from the horn 200, through the main body 400, down the diaphragm 600 and through the valve 612 into the container 1000 configured to engage a cap 800 for collecting and storing the expressed milk.

As further illustrated in FIGS. 3A-3D, the diaphragm 600 has a rim 602, a base 604, an upper wall 606, a lower wall 608 and is in a first initial state when a container 1000 is first attached to the main body 400 of the universal breast pump kit 100. The lower wall 608 of the valve 612 extend inwardly from the base 604 to define an aperture 610. The diaphragm 600 has a thick ring at both the top 602 and base 604 so that during the application of the negative pressure (or vacuum), the other components of the universal breast pump kit compresses around the thick rings in order to provide a seal. At the start of the milking operation, the diaphragm 600 and the container 1000 along with the cap 800 are removably connected with the lower portion 404 of the main body 400 thereby forming a single completed unit 100 for expressing milk.

Figure 4A:
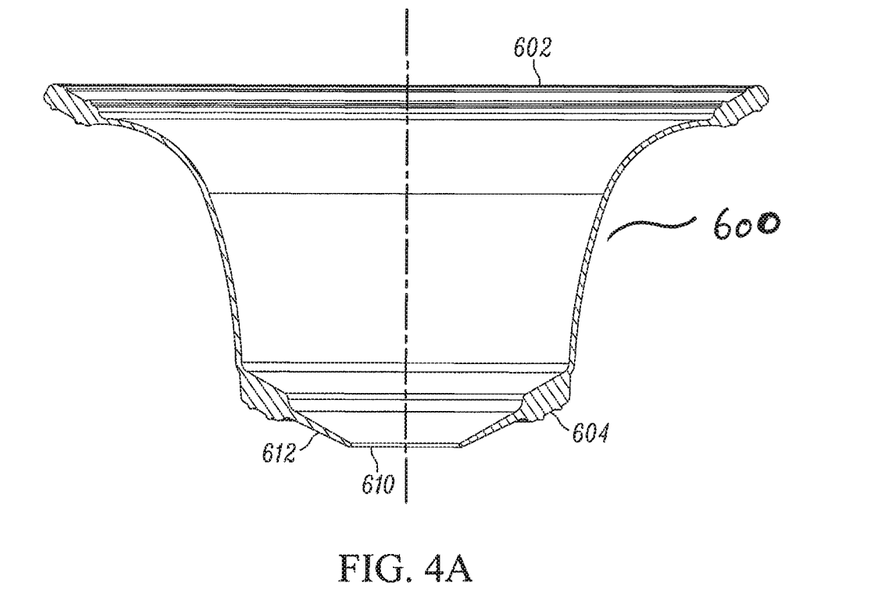
FIG. 4A is a sectional view of the diaphragm before start of the milking operation for one embodiment of the present disclosure.
Figure 4B:
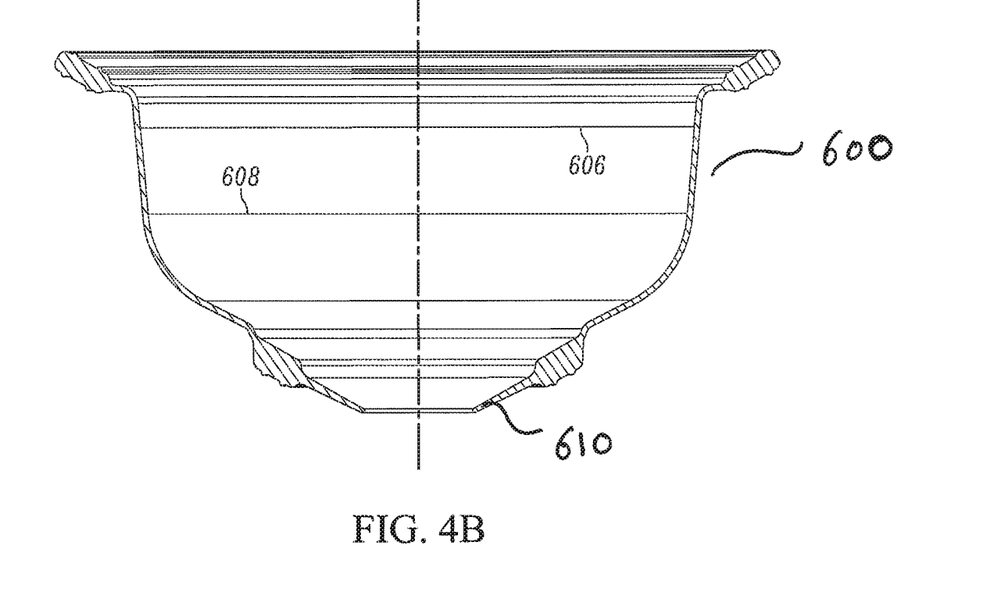
FIG. 4B is a sectional view of the diaphragm at maximum negative pressure during the milking operation for one embodiment of the present disclosure.

As illustrated in FIGS. 4A-4B, before the start of the pumping operation, the diaphragm 600 being in a first (non-expanded) state (FIG. 4A). During the milking operation, a negative pressure from the pressure source is communicated through the port 801 to the device 100 in order to create a suction on the funnel 202 for expressing the milk from the breast.

Figure 5A:
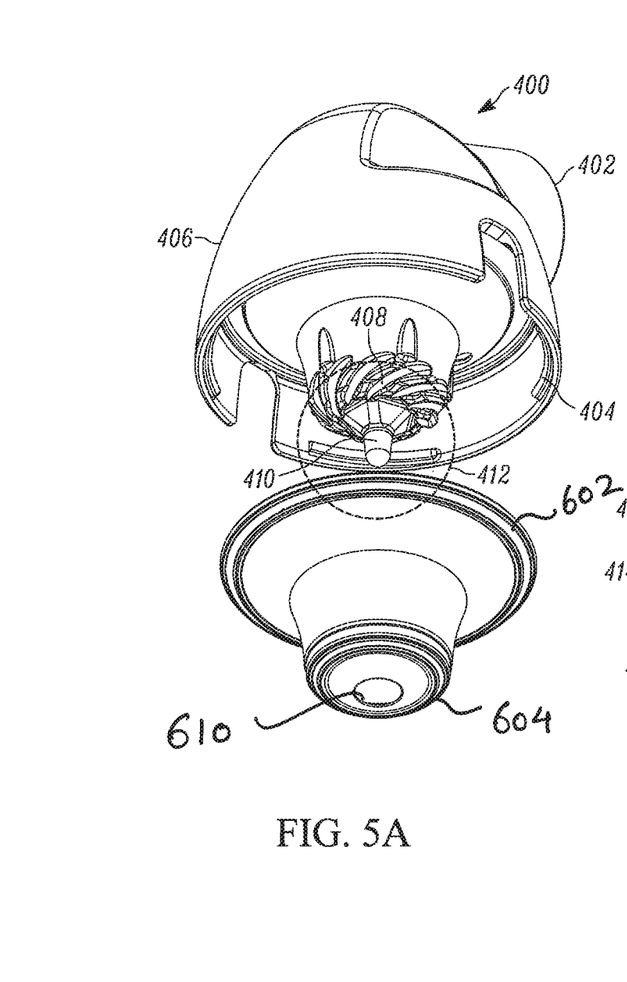
FIGS. 5A-5C is an illustration of an assembly of a main body and a diaphragm of one embodiment of the present disclosure.

FIG. 5A illustrates the main body 400 further comprising an internal surface having threads for engaging the cap 800 and the container 1000 used to collect the expressed breast milk. The rim 406 of the main body 400 includes a curved wall 408 that extends from the rim 406 downwardly and inwardly to the stem 410 at a distal end of the main body 400. The main body 400 further comprises a ribbed section 414 formed on a wall 412 adjacent the stem 410 having a round helical configuration 416. During operation, when negative pressure (or vacuum) is applied to the main body 400 through the port 401 of the main body, the rim 406 of the main body compresses the thick rings of the diaphragm 600, both at the top 602 and the base 604, thereby providing a seal contemporaneously with the seal formed by the aperture 610 of the diaphragm circumferentially engaging and sealing around the protruding stem 410 of the main body 400.

Figure 5B:
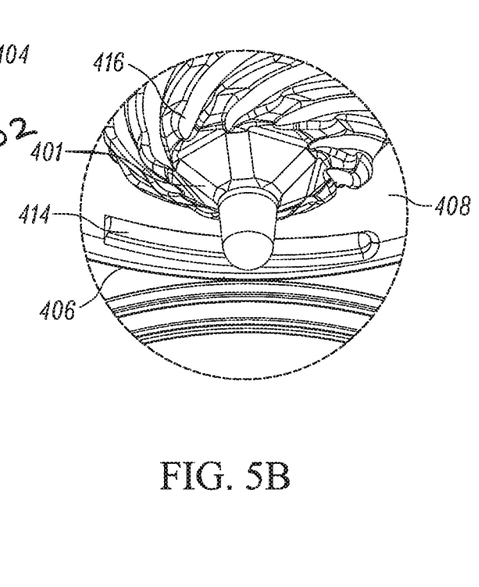
Figure 5C:
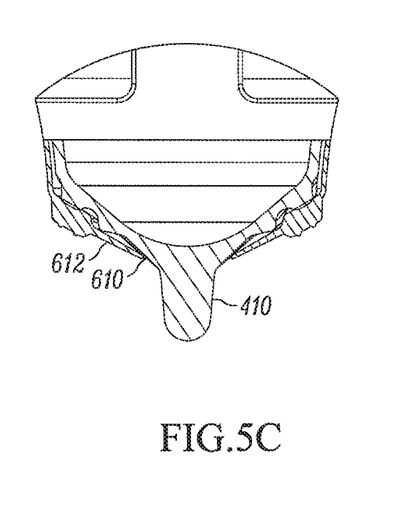

As further illustrated in FIGS. 5A-5C, in response to the negative pressure, the diaphragm 600 moves from the first state (FIG. 4A) to a second distended state (FIG. 4B) and the valve 612 circumferentially engages and seals around the stem 402 of the main body 400 to provide an airtight seal for pumping and collecting the expressed milk. Once the milking operation is completed and the negative pressure is released, the diaphragm 600 returns back to the first state (FIG. 4A) allowing the expressed milk to freely flow from the horn 200, through the main body 400, down the diaphragm 600 and through the valve into the container 1000.

Figure 6A:
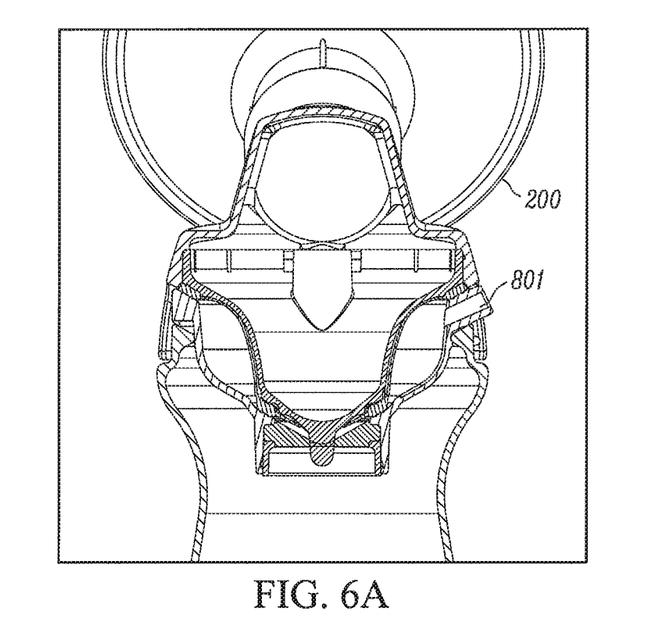
FIGS. 6A-6B is a sectional view of one embodiment of the universal breast pump device of the present disclosure during milking operation.
Figure 6B:
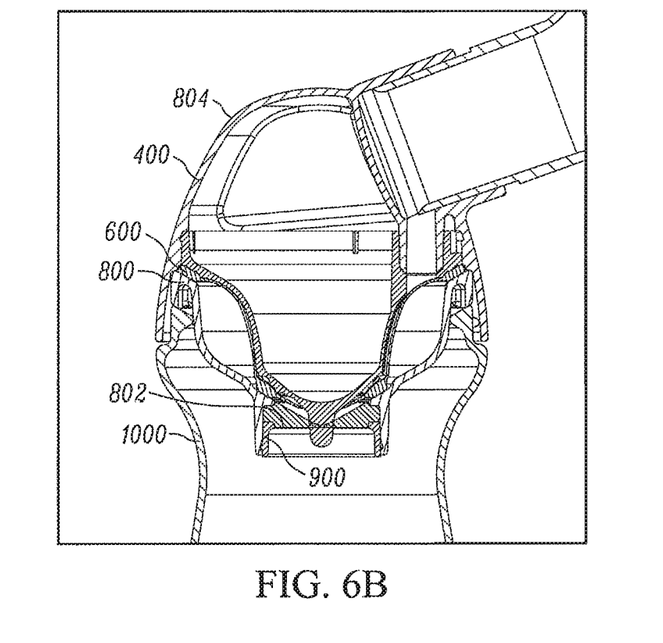

As shown in FIGS. 6A-6B, at the start of the milking operation, the diaphragm 600 and the container 1000 along with the cap 800 are removably connected with the lower portion 404 of the main body 400 thereby forming a single completed unit 100 for expressing milk. A gap is designed between the diaphragm 600 and the lower portion of the main body 404 (which projects without contact into the diaphragm 600). The gap is not uniform and is tapered to be thin at the top and larger closer to the stem 410 of the main body 400. The presence of the gap provides functionality to the diaphragm 600 in order to move expressed milk through the valve 612 portion of the universal breast pump device 100.

As further illustrated in FIGS. 6A-6B, a container 1000 configured to engage a cap 800 that has a built-in snap on feature to the container 1000. The cap 800 and the container 1000 are secured to the rest of the device 100 through threads on the main body 400 and container 1000. The cap 800 is designed with a seal 802, designed to be penetrable, as illustrated in FIG. 6B, in order to keep the milk contained within the container 1000. As further illustrated, when the cap 800 and the container 1000 are separated from the device 100, the seal 802 in the cap 800 stays in a closed position, thereby keeping the expressed milk collected in the container 1000 contained. Considering the amount of time it takes a user to operate the kit and collect the expressed milk, this self-sealing capability is a critical utility of the universal breast pump device 100. The cap has a rim 804 having a planar top portion 806 angled inwardly toward a center axis of the cap 800. As further illustrated, in another aspect of the present disclosure, the cap 800 is a self-sealing cap where a seal 802 is disposed within a wall contiguous with the shoulder of the cap and a retaining ring 900 is designed to retain the seal 802 against the shoulder. Further, a port 801 is positioned adjacent to the rim 804 and configured for connection to a pressure source during the milking operation.

While the particular preferred embodiments have been shown and described, it is obvious to those skilled in the art that changes and modifications may be made without departing from the teaching of the disclosure. The matter set forth in the foregoing description and accompanying drawings is offered by way of illustration only and not as limitation. The actual scope of the disclosure is intended to be defined in the following claims when viewed in their proper perspective based on the related art.

The invention claimed is:

1. A device for expressing milk from a breast, the device comprising:
   a horn having a funnel adapted for receiving a breast and a tube protruding downwards from the funnel and removably connected to a first end of a main body;
   the main body further comprising a lower second end having a stem extending therefrom;
   a diaphragm including a valve having a flexible wall extending inwardly from a base to define an aperture;
   a cap in communication with a pressure source and configured to engage with a container for receiving breastmilk, the container further configured to removably connect with the lower second end of the main body;
   wherein, at the start of the milking operation, when the diaphragm is disposed in a first state the valve is disengaged from the lower portion of the main body, and wherein the main body and the container are sealingly attached to form a single unit; and
   wherein, in response to a negative pressure from the pressure source, the diaphragm moves from the first state to a second distended state and the valve circumferentially engages and seals around the stem of the main body to provide an airtight seal during the milking operation, and wherein the main body further comprises, a dome shaped base having a rim; a curved wall having a helical rib extending from the rim downwardly and inwardly to the stem; and an internal surface adjacent to the rim having threads configured to engage the container.

2. The device of claim 1, wherein the diaphragm further comprises:
   a top side;
   a bottom side;
   a flexible membrane disposed between the top and the bottom side;
   wherein the flexible membrane is capable of expanding and contracting in response to a change of pressure from a pressure source.

3. The device of claim 2, wherein the top side and the bottom side have a thickness greater than the thickness of the flexible membrane.

4. The device of claim 1, wherein the container further comprises:
   an opening defined by a rim;
   an external surface adjacent to the rim having threads configured to engage with the main body.

5. The device of claim 1, wherein the cap further comprises:
   a rim having a planar top portion angled inwardly toward a center axis configured to removably attach with the container;
   an inner wall extending from the planar top portion to an annulus, wherein the inner wall has an opening formed adjacent the annulus;
   a ring wall extending from the annulus forming a shoulder adjacent the opening;
   a seal disposed within the ring wall contiguous with the shoulder;
   a clip to retain the seal against the shoulder; and
   a port positioned adjacent to the rim and configured for connection to a pressure source.

6. The device of claim 5, wherein the seal is a self-sealing seal made of self-sealing polymer.

7. The device of claim 1, wherein the funnel adapted for receiving the breast can vary in size to accommodate various users.

8. A method for expressing milk from a breast, comprising the steps of:
   configuring a horn having a funnel adapted for receiving a breast to engage with a first end of a main body;
   configuring a diaphragm including a valve having a flexible wall extending inwardly from a base to define an aperture to selectively engage with a lower second end of the main body having a stem extending therefrom;
   configuring a cap in communication with a pressure source to engage with a container for receiving breastmilk, wherein the container is further configured to engage with the lower second end of the main body, and wherein the main body further comprises; a dome shaped base having a rim; a curved wall having a helicle rib extending from the rim downwardly and inwardly to the stem; and an internal surface adjacent to the rim having threads configured to engage the container;

sealingly attaching the main body with the container to form a single unit at the start of the milking operation, the diaphragm being in a first state;

wherein, at the start of a milking operation in response to a negative pressure from the pressure source, the diaphragm is configured to move from the first state to a second distended state and, when the diaphragm is in the second distended state, the valve is configured to circumferentially engage and seal around the stem of the main body to provide an airtight seal during the milking operation; and wherein upon completion of the milking operation and release of the negative pressure, the diaphragm is configured to move back to the first state and in response thereto creating a gap between the valve and the stem of the main body and allowing the milk to flow from the horn through the main body and into the container.

9. A kit of parts for expressing milk from a breast, comprising:
   a horn having a funnel adapted for receiving a breast and a tube protruding downwards from the funnel and removably connected to a first end of a main body;
   the main body configured to engage with the horn and further comprising a lower second end having a stem extending therefrom;
   a diaphragm including a valve having a flexible wall extending inwardly from a base to define an aperture, wherein the valve is configured to engage with the main body;
   a cap in communication with a pressure source;
   a container configured to engage with the cap and further configured to removably connect with the lower second end of the main body, wherein the main body further comprises: a dome shaped base having a rim; a curved wall having a helical rib extending from the rim downwardly and inwardly to the stem; and an internal surface adjacent to the rim having threads configured to engage the container; and wherein
   during milking operation, the main body and the container are sealingly attached to form a single unit for expressing milk from a breast, and at the start of the milking operation, when the diaphragm is disposed in a first state, the valve is disengaged from the lower portion of the main body; and wherein, in response to a negative pressure from the pressure source, the diaphragm moves from the first state to a second distended state and the valve circumferentially engages and seals around the stem of the main body to provide an airtight seal during the milking operation.

10. A device for expressing milk from a breast, the device comprising:
    a horn having a funnel adapted for receiving a breast and a tube protruding downwards from the funnel and removably connected to a first end of a main body;
    the main body further comprising a lower second end having a stem extending therefrom;
    a diaphragm including a valve having a flexible wall extending inwardly from a base to define an aperture;
    a cap in communication with a pressure source and configured to engage with a container for receiving breastmilk, the container further configured to removably connect with the lower second end of the main body;
    wherein at the start of the milking operation, the diaphragm and the valve is removably connected with the lower portion of the main body, and wherein the main body and the container are sealingly attached to form a single unit and the diaphragm being in a first state; and
    wherein in response to a negative pressure from the pressure source, the diaphragm moves from the first state to a second distended state and the valve circumferentially engages and seals around the stem of the main body to provide an airtight seal during the milking operation, and wherein the cap further comprises: a rim having a planar top portion angled inwardly toward a center axis configured to removably attach with the container; an inner wall extending from the planar top portion to an annulus, wherein the inner wall has an opening formed adjacent the annulus; a ring wall extending from the annulus forming a shoulder adjacent the opening; a seal disposed within the ring wall contiguous with the shoulder; a clip to retain the seal against the shoulder; and a port positioned adjacent to the rim and configured for connection to the pressure source.

11. The device of claim 10, wherein the diaphragm further comprises:
    a top side;
    a bottom side;
    a flexible membrane disposed between the top and the bottom side;
    wherein the flexible membrane is capable of expanding and contracting in response to a change of pressure from the pressure source.

12. The device of claim 10, wherein the main body further comprises:
    a dome shaped base having a rim;
    a curved wall having a helical rib extending from the rim downwardly and inwardly to the stem; and
    an internal surface adjacent to the rim having threads configured to engage the container.

13. The device of claim 10, wherein the container further comprises:
    an opening defined by a rim;
    an external surface adjacent to the rim having threads configured to engage with the main body.

14. The device of claim 10, wherein the seal is a self-sealing seal made of self-sealing polymer.

15. The device of claim 12, wherein the top side and the bottom side have a thickness greater than the thickness of the flexible membrane.

16. The device of claim 10, wherein the funnel adapted for receiving the breast can vary in size to accommodate various users.

* * * * *